US006153391A

United States Patent [19]
Picksley et al.

[11] Patent Number: 6,153,391
[45] Date of Patent: Nov. 28, 2000

[54] INTERRUPTION OF BINDING OF MDM2 AND P53 PROTEIN AND THERAPEUTIC APPLICATION THEREOF

[75] Inventors: Steven Michael Picksley, Angus; David Philip Lane, Fife, both of United Kingdom

[73] Assignee: University of Dundee, Dundee, United Kingdom

[21] Appl. No.: 09/035,686

[22] Filed: Mar. 5, 1998

Related U.S. Application Data

[60] Division of application No. 08/424,957, Apr. 19, 1995, Pat. No. 5,770,377, which is a continuation-in-part of application No. 08/277,660, Jul. 20, 1994, Pat. No. 5,702,908.

[51] Int. Cl.$^7$ .................................................. G01N 33/53
[52] U.S. Cl. .............................. 435/7.1; 514/12; 514/13; 514/14; 514/15; 514/16; 514/17; 530/324; 530/325; 530/326; 530/317; 530/328; 530/329; 530/330
[58] Field of Search ......................... 514/12–17; 435/7.1; 530/324–330

[56] References Cited

U.S. PATENT DOCUMENTS

| | | | |
|---|---|---|---|
| 5,532,348 | 7/1996 | Huibregtse et al. | 536/23.5 |
| 5,550,023 | 8/1996 | Kinzler et al. | 435/7.1 |

FOREIGN PATENT DOCUMENTS

| | | |
|---|---|---|
| 9320238 | 10/1993 | WIPO . |
| 08241 | 4/1994 | WIPO . |

OTHER PUBLICATIONS

Barak, Y., T al., "mdm2 expression is induced by wild type p53 activity," EMBO Journ., 12:461–468 (1993).
Barak, Y. & M. Oren, "Enhanced binding of a 95 kDa protein to p53 in cells undergoing p53–mediated growth arrest," EMBO Journ., 11:2115–2121 (1992).
Brown, D. R., et al., "The Tumor Suppressor p53 and the Oncoprotein Simian Virus 40 T Antigen Bind to Overlapping Domains on the MDM2 Protein," Molec. Cell. Biol., 13:6849–6857 (1993).
Cahilly–Snyder, L., et al., "Molecular analysis and chromosomal mapping of amplified genes isolated from a transformed mouse 3T3 cell line," Somatic Cell and Molecular Genetics, 13:235–244 (1987).
Chen, J., et al., "Mapping of the p53 and mdm–2 interaction domains," Mol. Cell. Biol., 13:4107–4114 (1993).
Dyson, N., et al., "Adenovirus E1A Makes Two Distinct Contacts with the Retinoblastoma Protein," J. Virol., 66:4606–4611 (1992).
Dyson, N., et al., "Homologous Sequences in Adenovirus E1A and Human Papillomavirus E7 Proteins Mediate Interaction with the Same Set of Cellular Proteins," J. Virol., 66:6893–6902 (1992).
Farmer, G., et al., "Wild–Type p53 activates transcription in vitro," Nature, 358:83–86 (1992).

Funk, W. D., et al., "A transcriptionally active DNA–binding site for human p53 protein complexes," Mol. Cell. Biol., 12:2866–2871 (1992).
Kern, S. E., et al., "Oncogenic forms of p53 inhibit p53–regulated gene expression," Science, 256:827–830 (1992).
Michalovitz, D., et al., "Conditional inhibition of transformation and of cell proliferation by a temperature–sensitive mutant of p53," Cell, 62:671–680 (1990).
Momand, J., et al., "The mdm–2 oncogene product forms a complex with the p53 protein and inhibits p53 mediated transactivation," Cell, 69:1237–1245 (1992).
Oliner, J. D., et al., "Oncoprotein mdm2 conceals the activation domain of tumour suppressor p53," Nature, 362:857–860 (1993).
Unger, T., et al., "p53: A transdominant regulator or transcription whose function is ablated by mutations occurring in human cancer," EMBO Journ., 11:1383–1390 (1992).
Picksley, S.M. & D.P. Lane, "The p53–mdm2 autoregulatory feedback loop: A paradigm for the regulation of growth control by p53?" BioEssays, 15:689–690 (1993).
Lin, J. et al., "Several hydrophobic amino acids in the p53 amino–terminal domain are required for transcriptional activation, binding to mdm–2 and the adenovirus 5 E1B 55–kD protein," Genes & Develop., 8:1235–1246 (1994).
Schlichtholtz, B., et al., "The Immune Response to p53 in Breast Cancer Patients is Directed Against Immunodominant Epitopes Unrelated to Mutational Hot Spot," Canc. Res., 52:6380–6384 (1993).
Wu, X., et al., "The p53–mdm2 autoregulatory feedback loop," Genes & Develop., 7:1126–1132 (1993).
Picksley, S. M., et al., "Immunochemical analysis of the interaction of p53 with MDM2;—fine mapping of the MDM2 binding site on p53 using synthetic peptides," Oncogene, 9:2523–2529 (1994).
Deffie, A., et al., "The tumor suppressor p53 regulates its own transcription," Mol. Cell. Biol., 13:3415–2423 (1993).
Liu, X., et al., "The p53 activation domain binds the TATA box–binding polypeptide in holo–TFIID, and a neighboring p53 domain inhibits transcription," Mol. Cell. Biol., 13:3291–3300 (1993).
Oliner, J.D., et al., "Amplification of a gene encoding a p53–associated protein in human sarcomas," Nature, 358:80–83 (1992).

(List continued on next page.)

*Primary Examiner*—Sheela Huff
*Attorney, Agent, or Firm*—Flehr Hobach Test Albritton & Herbert LLP

[57] ABSTRACT

A method for interfering with the binding between p53 and MDM2 or a protein having a p53 binding site analogous to that of MDM2, which method comprises administering a effective amount of a compound, selected from the group consisting of a peptide having up to twenty eight amino acids which is able to disrupt or prevent binding between p53 and MDM2, or a functional peptide analogue thereof.

Compounds for use in the method, methods for detecting such compounds and their application in the diagnosis and treatment of tumors is also described and claimed.

12 Claims, 9 Drawing Sheets

OTHER PUBLICATIONS

Lane, D., et al., Overheads presented in conjunction with talk given Oncogenes EMBL Symposium at Heidelberg on Apr. 20, 1994.

Picksley, S. M. and D. P. Lane, "p53 and Rb: their cellular roles", Current Opinion in Cell Biology 6:853–858 (1994).

Martin, K., et al., "Stimulation of E2F1/DP1 Transcriptional Activity by MDM2 Oncoprotein," Natue 375:691–698 (1995).

Marston, N.J., et al., "Interaction of p53 with MDM2 is Independent of E6 and Does Not Mediate Wild Type Transformation Suppressor Function," Oncogene 9:2707–2716 (1994).

Lane, D.P., et al., "On the Regulation of the p53 Tumour Suppressor, and its Role in the Cellular Response to DNA Damage," Phil. Trans. R. Soc. Lond. B 347:83–87 (1995).

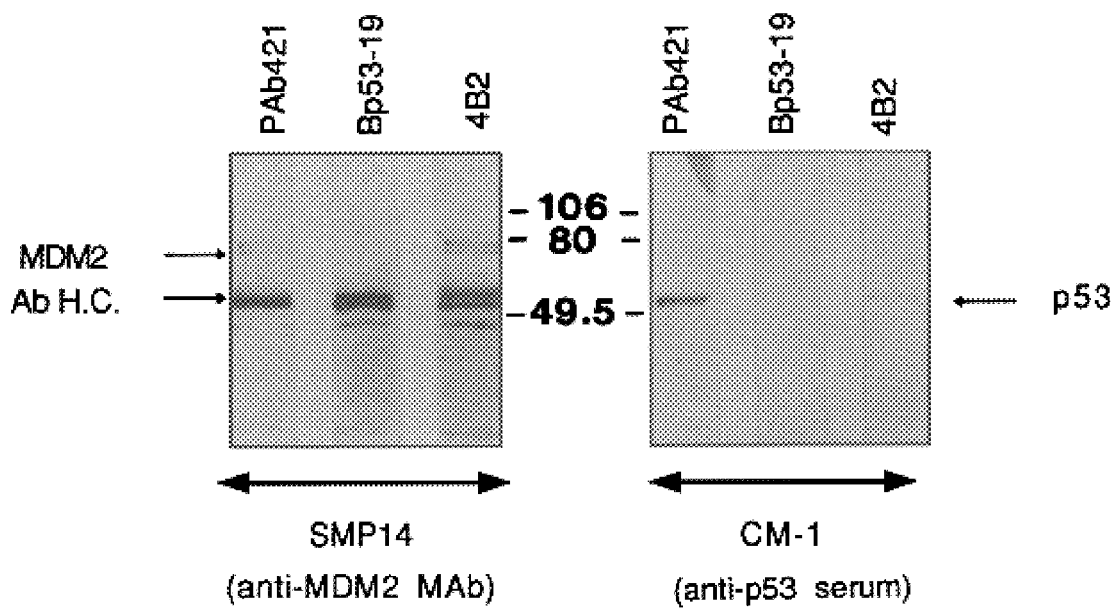

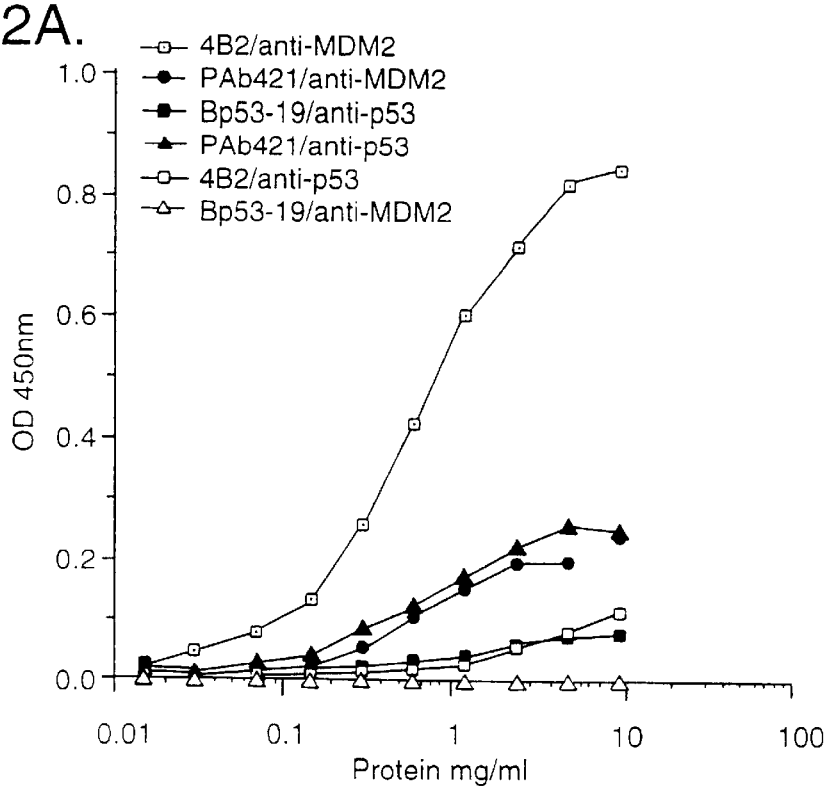
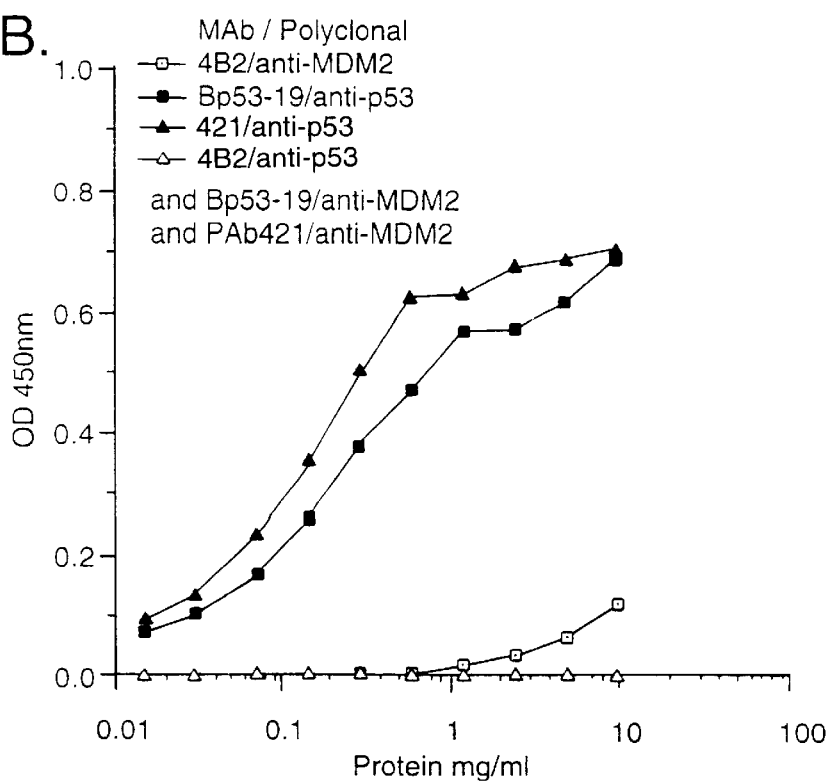

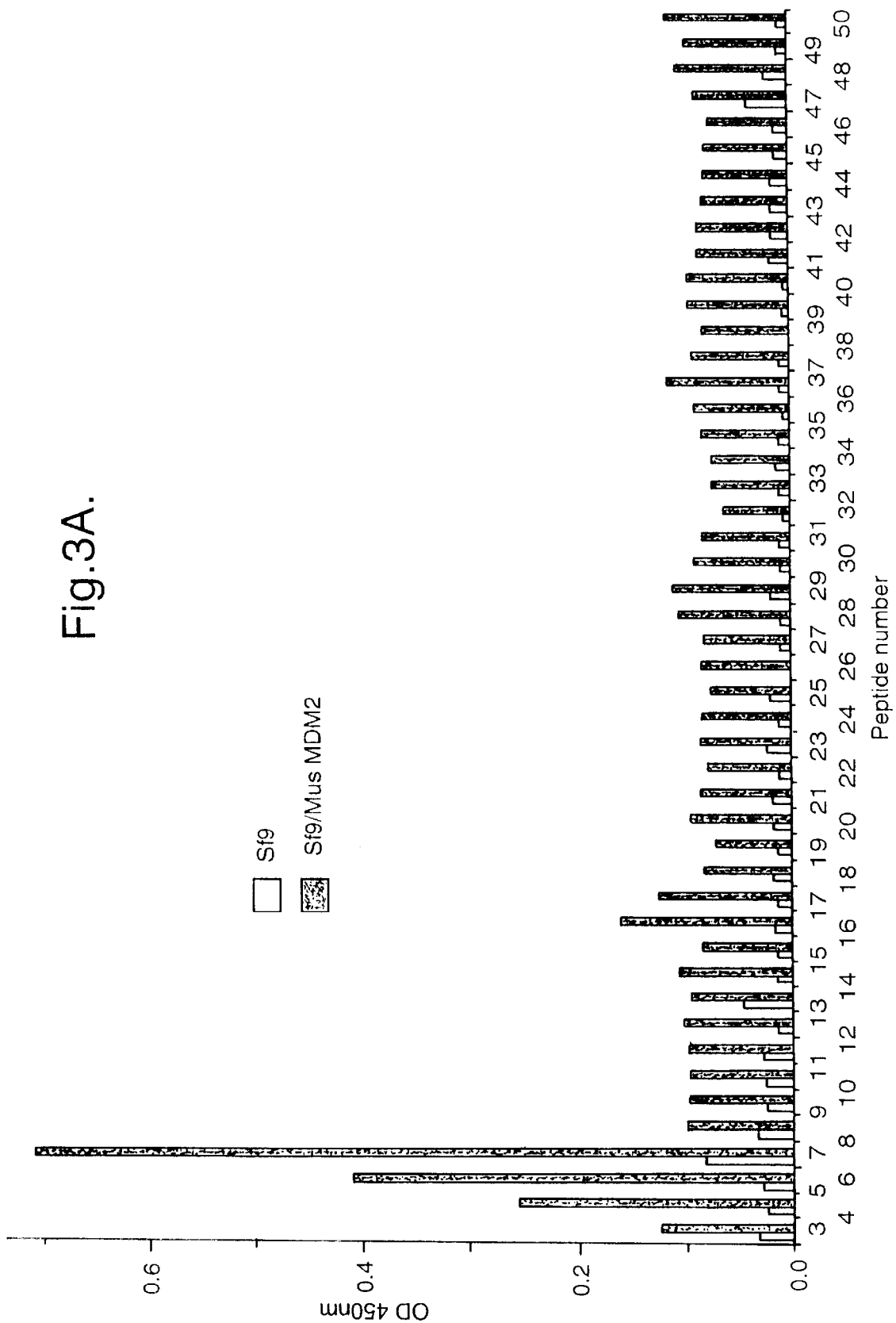

| | | |
|---|---|---|
| #5 | 11  EPPLSQETFSDLWKL  25 | HUMAN p53 SEQUENCE |
| #6 | 16  QETFSDLWKLLPENN  30 | |
| #83 | 13  PLSQETFSGLWKLLP  27 | MOUSE p53 SEQUENCE |
| #84 | 18  TFSGLWKLLPPEDIL  32 | |

CONSENSUS MDM2 BINDING SITE    -QETFSD/GLWKL-

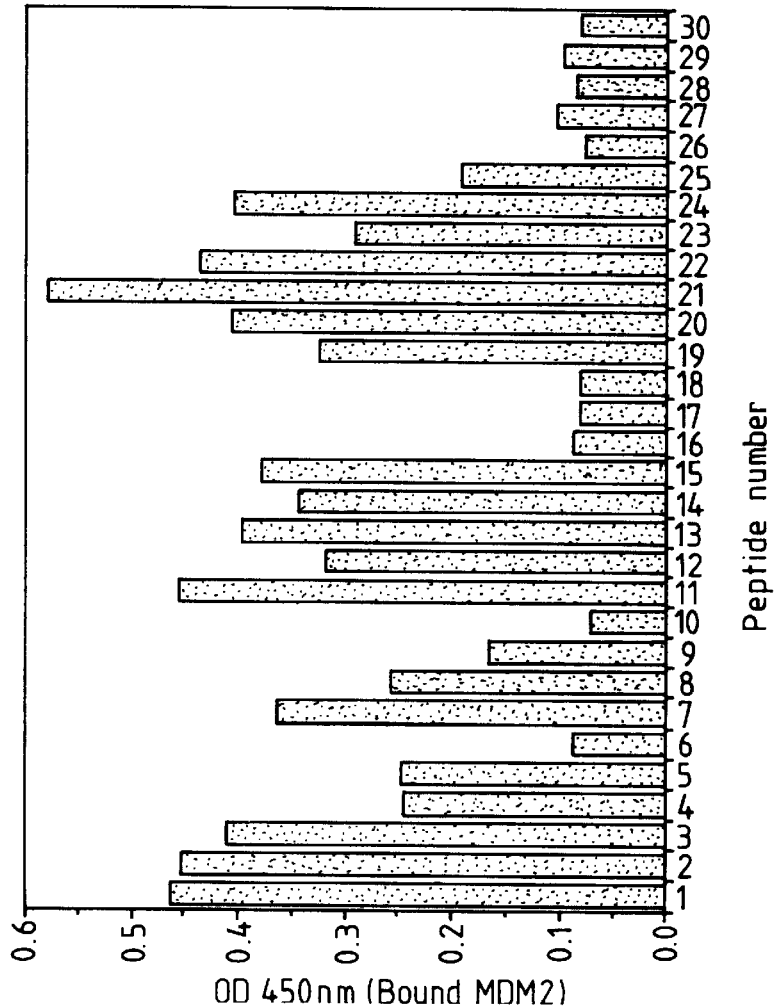

Fig.6.
Further information on the key residues required for MDM2 binding

| NO. | PEPTIDE | CHANGE |
|---|---|---|
| 1. | SQETFSDLWKL | – |
| 2. | AQETFSDLWKL | S TO A |
| 3. | SAETFSDLWKL | Q TO A |
| 4. | SQATFSDLWKL | E TO A |
| 5. | SQEAFSDLWKL | T TO A |
| 6. | SQETASDLWKL | F TO A |
| 7. | SQETFADLWKL | S TO A |
| 8. | SQETFSALWKL | D TO A |
| 9. | SQETFSDAWKL | L TO A |
| 10. | SQETFSDLAKL | W TO A |
| 11. | SQETFSDLWAL | K TO A |
| 12. | SQETFSDLWKA | L TO A |
| 13. | DQETFSDLWKL | S TO D |
| 14. | SQETFDDLWKL | S TO D |
| 15. | SQESFSDLWKL | T TO S |
| 16. | SQETISDLWKL | F TO I |
| 17. | SQETLSDLWKL | F TO L |
| 18. | SQETMSDLWKL | F TO M |
| 19. | SQETFTDLWKL | S TO T |
| 20. | SQETFPDLWKL | S TO P |
| 21. | SQETFSELWKL | D TO E |
| 22. | SQETFSQLWKL | D TO Q |
| 23. | SQETFSNLWKL | D TO N |
| 24. | SQETFSDMWKL | L TO M |
| 25. | SQETFSDIWKL | L TO I |
| 26. | SQETFSDLRKL | W TO R |
| 27. | SQETFSDLFKL | W TO F |
| 28. | SQETFSDLYKL | W TO Y |
| 29. | SQETFSFLIKL | TAg core seq. |
| 30. | TAg first 15aa | |

Fig. 7.

Biotinylated peptide containing MDM2 binding site of p53 added to streptavidin-coated plate

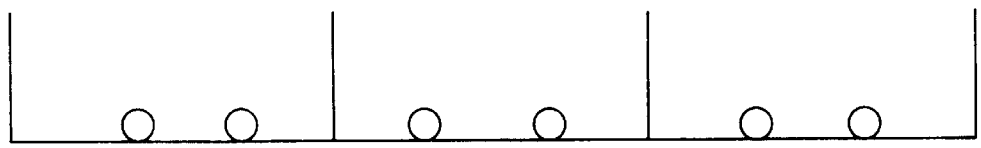

Add MDM2 (peptide or polypeptide) in solution + or − test agents

| No agent | + test agent 1 | + test agent 2 |

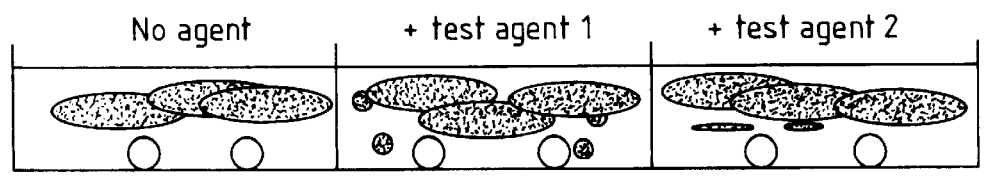

Wash away unbound MDM2. Determine bound MDM2 by ELISA

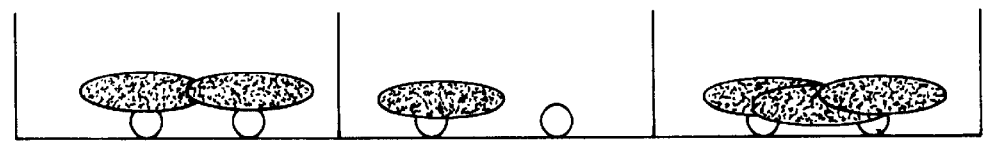

ELISA reading
++
(reference)

+
(below reference)
Test agent disrupts
p53-MDM2 interaction

+++
(above reference)
Test agent enhances
p53-MDM2 interaction

INTERRUPTION OF BINDING OF MDM2 AND P53 PROTEIN AND THERAPEUTIC APPLICATION THEREOF

This is a division of application Ser. No. 08/424,957 filed Apr. 19, 1995, now U.S. Pat. No. 5,770,377, issued Jun. 23, 1998, which was a continuation-in-part of application Ser. No. 08/277,660, filed Jul. 20, 1994, now U.S. Pat. No. 5,702,908.

FIELD OF THE INVENTION

The invention relates to the area of cancer detection and therapeutics. More particularly it relates to the prevention or disruption of the inactivation of the p53 tumour suppressor which occurs as a result of the binding of a protein through the amino acid motif within the region of p53 represented by amino acids 16–30 QETFSDLWKLLPENN (SEQ ID NO:1) of the human p53 protein. An example of such a protein is the oncogene protein MDM2 (human MDM2).

BACKGROUND OF THE INVENTION

Inactivation of the p53 tumour suppressor is a frequent event in human neoplasia. The inactivation can occur by mutation of the p53 gene or through binding to viral or cellular oncogene proteins, such as the SV40 large T antigen and MDM2. While the mechanism through which wild-type p53 suppresses tumour cell growth is as yet poorly defined it is clear that one key feature of the growth suppression is the property of p53 to act as a transcription factor (Farmer, G., et al. (1992). Nature, 358, 83–86; Funk, W. D. et al. (1992). Mol. Cell. Biol., 12, 2866–2871; Kern, S. E., et al. (1992). Science, 256, 827–830). Currently, considerable effort is being made to identify growth control genes that are regulated by p53 binding to sequence elements near or within these genes. A number of such genes have been identified. In cases such as the muscle creatine kinase gene (Weintraub, H., et al. (1991). Proc. Natl. Acad. Sci. U.S.A., 88, 4570–4571; Zambetti, G. P., et al. (1992). Genes Dev., 6, 1143–1152) and a GLN retroviral element (Zauberman, A., et al. (1993). Embo J., 12, 2799–2808) the role these genes might play in the suppression of growth control is unclear. Yet there are other examples, namely mdm2 (Barak, Y., et al. (1993). Embo J., 12, 461–468; Wu, X., et al. (1993). Genes Dev., 7, 1126–1132) GADD 45 (Kastan, M. B., et al. (1992). Cell, 71, 587–597) and WAF1 or CIP1 (El-Beiry, W. S., et al. (1993). Cell, 75, 817–825; Harper, J. W., et al. (1993). Cell., 75, 805–816) where their involvement in the regulation of cell growth is better understood.

In the present text "mdm2" refers to the oncogene and "MDM2" refers to the protein obtained as a result of expression of that gene.

Mdm2, a known oncogene, was originally found on mouse double minute chromosomes (Cahilly-Snyder., L., et al. (1987) Somatic Cell Mol. Genet. 13, 235–244). Its protein product was subsequently found to form a complex with p53, which was first observed in a rat fibroblast cell line (Clone 6) previously transfected with a temperature sensitive mouse p53 gene (Michalovitz, D., et al. (1990). Cell, 62, 671–680). The rat cell line grew well at 37° C. but exhibited a G1 arrest when shifted down to 32° C., which was entirely consistent with an observed temperature dependent switch in p53 conformation and activity. However, the p53-MDM2 complex was only observed in abundance at 32° C., at which temperature p53 was predominantly in a functional or "wild-type" form (Barak, Y. et al. (1992). Embo J., 11, 2115–2121 and Oren, 1992; Momand, J., et al. (1992). Cell, 69, 1237–1245). By shifting the rat cell line down to 32° C. and blocking de novo protein synthesis it was shown that only "wild-type" p53 induced expression of the mdm2 gene, thereby accounting for the differential abundance of the complex in terms of p53 transcriptional activity (Barak, Y., et al. (1993). Embo J., 12, 461–468) The explanation was further developed by the identification of a DNA binding site for wild-type p53 within the first intron of the mdm2 gene (Wu, X., et al. (1993). Genes Dev., 7, 1126–1132). Reporter constructs employing this p53 DNA binding site revealed that they were inactivated when wild-type p53 was co-expressed with MDM2.

This inhibition of the transcriptional activity of p53 may be caused by MDM2 blocking the activation domain of p53 and/or the DNA binding site. Consequently, it was proposed that mdm2 expression is autoregulated, via the inhibitory effect of MDM2 protein on the transcriptional activity of wild-type p53. This p53-mdm2 autoregulatory feedback loop provided a novel insight as to how cell growth might be regulated by p53. Up to a third of human sarcomas are considered to overcome p53-regulated growth control by amplification of the mdm2 gene (Oliner, J. D., et al. (1992). Nature, 358, 80–83). Hence the interaction between p53 and MDM2 represents a key potential therapeutic target.

The cDNA sequence encoding the human MDM2 protein (which is also referred to as "HDM2" in the art) is known from WO93/20238. This application also discloses that human MDM2 protein binds with human p53 and it has been suggested that molecules which inhibit the binding of MDM2 to p53 would be therapeutic by alleviating the sequestration of p53. However it is also suggested that the p53 and MDM2 binding site is extensive, including amino acid residues 13–41 of p53 as well an additional nine to thirteen residues at either the amino or carboxyl terminal side of the peptide are also involved. This would indicate that a large polypeptide or other large molecule would be required in order to significantly interfere with the binding.

The applicants have therefore sought to immunochemically characterize the p53-MDM2 complex, and also determine in fine detail the MDM2 binding site on p53.

Surprisingly, it has been found that only a relatively small number of amino acids within the p53 protein are involved in binding to MDM2.

SUMMARY OF THE INVENTION

The precise identification of this binding site is vital to allow the rational design of molecules which will disrupt or prevent binding between p53 and MDM2 or proteins containing analogous p53 binding sites. In addition it allows for the design of screening procedures which will enable compounds which can disrupt or prevent the binding interaction to be accurately and rapidly identified.

The applicants have found that the site on the p53 protein which is responsible for binding to MDM2 is a small sequence of only six amino acids, of which three amino acids have been found to be critical. This sequence is represented by the sequence TFSDLW (SEQ ID NO:2) in human (amino acids 18–23 in the sequence) and TFSGLW (SEQ ID NO:3) (amino acids 18–23) in mouse, of which the critical amino acids appear to be F–LW. By disrupting or preventing p53 from binding in this specific region, the deleterious effects of binding to MDM2 or proteins having an analogous p53 binding site can be avoided. Proteins having a p53 binding site which is analogous to that of MDM2 will generally comprise oncogene proteins which bind to p53 through the amino acid motif within the region of p53 represented by amino acids 16-30 (QETFSDLWKLLPENN) (SEQ ID NO:1) of the human p53 protein.

This finding has recently been reinforced by a report that two components of the transcriptional machinery, namely TAFII140 and TAFII60, require Leu-22 and Trp-23 for them to bind to p53 and mediate p53 transcriptional activity (Thut-CJ, et al., 1995, Science 267:100–4). The same two amino acids of p53 are critical for the binding of MDM2 as disclosed above as well as Ad E1b, thus strengthening the hypothesis that MDM2 and E1b act by binding to p53 and blocking the transcriptional activity of p53.

Hence the present invention provides a method for interfering with the binding between p53 and MDM2 or an oncogene protein having an analogous p53 binding site, which method comprises administering a effective amount of a compound, selected from the group consisting of a peptide having up to twenty eight amino acids which is able to disrupt or prevent the binding between p53 and MDM2, or a functional peptide analogue thereof.

It may be expected that small peptides, for example of from 4 to 10 amino acids, suitably from five to 10 amino acids, or peptide analogues thereof would be particularly suitable in such a process. Peptides which would be of particular interest are those which show a consensus with the fragment of p53 which has been found to be crucial for binding. Such peptides include fragments of p53 protein which includes at least some of amino acids 18–23 within the sequence of human p53, as identified in WO93/20238 or a peptide analogue thereof. Suitably these peptides are those which are circular, linear or derivatised to achieve better penetration of membranes.

Novel peptides or peptide analogues of this type form a further aspect of the invention.

Hence preferred peptides include the sequence FxxLW (SEQ ID NO:4) such as TFSDLW (SEQ ID NO: 2) or a portion thereof. As used herein, 'x' refers to any amino acid. In a preferred embodiment, an aspartate residue in the sequence is replaced by a glutamate residue so that the sequence is FXELW (SEQ ID NO:5) such as TFSELW (SEQ ID NO:6).

Other compounds which may interfere with the binding include organic compounds which are modelled to achieve the same three dimensional structure as the said region of the p53 peptide. Hence in an alternative embodiment the invention provides an organic compound which is modelled to resemble the three dimensional structure of the amino acids represented by the sequence F–LW (SEQ ID NO:4) as it appears in human p53 in the region of amino acids 19–23 and which binds to human MDM2. In particular the organic compound may be modelled to resemble the three dimensional structure of the sequence TFSDLW as it appears in the region of amino acides 18–23 of human p53.

A suitable oncogene protein is MDM2 but the disruption of binding of p53 to other oncogene proteins containing a p53 binding site analogous to that of MDM2 are included within the scope of the present invention. Examples of other such oncogene proteins include the adenovirus EIB 58kD protein, the Tata box binding protein TBP and the transcription factor of the E2F family.

As used herein the expression 'peptide analogue' prefers to peptide variants or organic compounds having the same functional activity as the peptide in question, in particular which interfere with the binding between p53 and MDM2. Examples of such analogues will include chemical compounds which are modelled to resemble the three dimensional structure of the sequence TFSDLW (SEQ ID NO:2) and in particular the arrangement of the F–LW (SEQ ID NO:4) amino acids as they appear in human p53, which compounds bind to human MDM2.

Suitable modelling techniques are known in the art. This includes the design of so-called 'mimetics' which involves the study of the functional interactions of the molecules and the design of compounds which contain functional groups arranged in such a manner that they could reproduce those interactions.

The designing of mimetics to a known pharmaceutically active compound is a known approach to the development of pharmaceuticals based on a "lead" compound. This might be desirable where the active compound is difficult or expensive to synthesise or where it is unsuitable for a particular method of administration, eg peptides are unsuitable active agents for oral compositions as they tend to be quickly degraded by proteases in the alimentary canal. Mimetic design, synthesis and testing is generally used to avoid randomly screening large number of molecules for a target property.

There are several steps commonly taken in the design of a mimetic from a compound having a given target property. Firstly, the particular parts of the compound that are critical and/or important in determining the target property are determined. In the case of a peptide, this can be done by systematically varying the amino acid residues in the peptide, eg by substituting each residue in turn. These parts or residues constituting the active region of the compound are known as its "pharmacophore".

Once the pharmacophore has been found, its structure is modelled to according its physical properties, eg stereochemistry, bonding, size and/or charge, using data from a range of sources, eg spectroscopic techniques, X-ray diffraction data and NMR. Computational analysis, similarity mapping (which models the charge and/or volume of a pharmacophore, rather than the bonding between atoms) and other techniques can be used in this modelling process.

In a variant of this approach, the three-dimensional structure of the ligand and its binding partner are modelled. This can be especially useful where the ligand and/or binding partner change conformation on binding, allowing the model to take account of this the design of the mimetic.

A template molecule is then selected onto which chemical groups which mimic the pharmacophore can be grafted. The template molecule and the chemical groups grafted on to it can conveniently be selected so that the mimetic is easy to synthesise, is likely to be pharmacologically acceptable, and does not degrade in vivo, while retaining the biological activity of the lead compound. The mimetic or mimetics found by this approach can then be screened to see whether they have the target property, or to what extent they exhibit it. Further optimisation or modification can then be carried out to arrive at one or more final mimetics for in vivo or clinical testing.

In order to identify compounds which are useful in the above described methods, compounds may be screened for interference of the MDM2/p53 interaction. Suitably screening methods would be based upon observations with regard to compounds which interfere with the binding between peptides which comprise or represent the binding site of an oncogene protein such as MDM2 and p53, based upon the information regarding said binding site given herein. Such methods include immunoassay techniques such as radioimmunoassay (RIA) and enzyme linked immunoabsorbent assay (ELISA) which are well known in the art. Particularly suitable techniques are competitive assay techniques where a peptide or reagent which either is or represents one of the peptides or reagents which either is or represents either p53 or the oncogene protein is exposed to a compound under test and the other one of the peptides or reagents which either is or represents either p53 or the oncogene protein. The presence of bound complex is then detected. This may be achieved either by labelling of the said one of said peptides or reagent for example using a gold or other visible label, or by administering a labelled antibody or sequence of antibodies, one of which includes a label, in a conventional manner. Suitable antibodies for example for MDM2 and p53 are described herein. Suitably one of the peptides or reagents representing p53 or the oncogene protein is immobilised on a support.

Hence the invention further provides a method of identifying compounds which interfere with the binding of human MDM2 to human p53,said method comprising immobilising a first peptide molecule,
adding a compound to be tested and a second peptide molecule; detecting the presence of bound second peptide at the immobilisation site;

wherein one of the first peptide or second peptide is MDM2 or an oncogene protein having a p53 binding site analogous to that of MDM2 or a fragment thereof which includes said binding site, and the other is a fragment of human p53 of from five to twenty eight amino acids including the amino acid residues FxxLW (SEQ ID NO:4) or a peptide analogue thereof.

A immunoassay for detecting binding is illustrated hereinafter.

A biotinylated peptide containing the MDM2 binding site fo p53 from amino acids 16–25 (or smaller peptides as described above containing for example TFSDLW) (SED ID NO:2) would be immobilised on a streptavidin coated ELISA plate. Recombinant MDM2 protein would be added to these ELISA plates in the presence of absence of test compounds or agents. This would then be incubated for 2 hours at 4° C. Bound MDM2 would be detected by a standard ELISA procedure. The inhibitory or stimulatory effect of these reagents would be determined by reference to control wells in which no such test compounds were included. Further experimental details are as described hereinafter and the binding assay is illustrated in FIG. 7.

The invention includes quantitative assays. For example there is provided a method of identifying compounds which interfere with the binding of human MDM2 to human p53, said method comprising binding a predetermined quantity of a first peptide which is detectably labelled to a peptide, adding a compound to be tested; and determining the quantity of the first protein which is displaced from or prevented from binding to the second peptide, wherein one of the first peptide or the second peptide is MDM2 or a peptide having a p53 binding site analogous to that of MDM2, and the other is a fragment of human p53 of from six to twenty eight amino acids including the amino acid residues 18–23 in the sequence of human p53 as set out in WO93/20238, or a peptide analogue thereof.

Assays which include fragments of p53 including the MDM2 binding site as characterised above, or peptide analogues thereof form a further part of the invention. The assay may be formulated as a kit which also forms part of the invention. A particularly useful form of the assay would be one which was adapted to test levels of oncogene protein in biological samples. Such a kit would comprise a fragment of p53 or a peptide analogue as binding agent thereof together with an antibody which is specific for the oncogene protein such as MDM2. Alternatively antibodie(s) able to detect bound complex may be included in the kit.

This could be used in diagnosis to measure the levels of oncogene protein or MDM2 in blood samples in the case of leukaemias or solid carcinomas such as sarcomas and glioblastomas.

Suitably in the above described assay methods, the oncogene protein is human MDM2 and the other protein comprises a fragment of human p53 of from 12 to 28 amino acids including the sequence TFSDLW (SEQ ID NO:2).

The methods can be readily adapted to provide a high throughput screen, for example by carrying out the process in a 96-well format. Automated screening techniques can be applied in these circumstances as would be understood in the art. Compounds from various sources can be screened in large numbers. One potential source of compounds are the available synthetic combinatorial peptide libraries.

The use of compounds identified by this screening method in the treatment of tumours forms a further aspect of the invention.

Methods of treatment of conditions such as cancer and other malignancies are envisaged by the administration of the compounds of the invention.

Hence the invention also provides a method for inhibiting the growth of tumour cells which contain a human MDM2 gene amplification which method comprises administering a effective amount of a compound which interferes with the binding between pS3 and an MDM2, said compound being selected from the group consisting of a peptide having up to twenty eight amino acids which is able to disrupt or prevent the binding between p53 and MDM2, or a functional peptide analogue thereof.

Preferably in the above-described method of treatment, the compound is a peptide of from six to twenty eight amino acids which has a consensus with a region of human p53 and includes the sequence FxxLW (SEQ ID NO:4) for example TFSDLW (SEQ ID NO:2).

Alternatively, the compound used in the method is peptide analogue such as an organic compound which binds to the same site on MDM2 as the sequence TFSDLW (SEQ ID NO:2).

For use in these applications, the compounds are suitably applied in the form of compositions with pharmaceutically acceptable carriers. These may be solid or liquid for carriers and the compositions suitable for oral or parenteral application as would be understood in the art. Dosages of the compounds will depend upon the patient, the particular condition and the nature of the specific compound chosen. For example, when the compound is a peptide fragment dosages of from 0.1 to 10 mg/Kg may be effective.

It has been suggested (Picksley and Lane. (1993). Bioessays. 15, 10, 689–690) that mdm2 expression is autoregulated in a feedback loop, via the inhibitory effect of MDM2 protein on the transcriptional activity of wild-type p53. Any interference with the binding between p53 and MDM2 in accordance with the present invention, will affect the p53-MDM2 autoregulatory loop. Given p53's role as guardian of the genome, compounds which have such an effect could enhance the activity of other therapeutic agents.

Hence in a further aspect the invention comprises a pharmaceutical composition comprising synergistic amount of a compound of the invention in combination with another anticancer therapeutic agent.

DNA encoding an MDM2-binding, p53 derived peptide, or multiple copies thereof may also be administered to tumour cells as a mode of administering the peptide. Hence the invention provides a method for inhibiting the growth of tumour cells which contain a human MDM2 gene amplification, the method comprising applying to said tumour cells a DNA molecule which expresses a polypeptide comprising a portion of p53 or a variant thereof, said portion comprising amino acids 18–23 of p53, said polypeptide being capable of binding to human MDM2.

The DNA will typically be in an expression construct, such as a retrovirus, DNA virus, or plasmid-vector, which has the DNA elements necessary for expression properly positioned to achieve expression of MDM2-binding peptide. The DNA can be administered inter alia encapsulated in liposomes, or in any other form known to the art to achieve efficient uptake by cells.

By identifying the binding site so specifically, the applicants have opened up the possibility of making small therapeutic compounds which will target this site specifically. This is advantageous since small molecules are more likely to be able to penetrate into a cell and hence be therapeutically active. Furthermore the diagnostic process can be effected more accurately and using simpler molecules as a result of this discovery.

BRIEF DESCRIPTION OF THE DRAWINGS

FIGS. 1A–1B show Western blots of immunoprecipitates of MDM2, p53 and the MDM2-p53 complex obtained from Clone 6 cells.

FIGS. 2A–2B are graphs showing the results of two-site immunoassays to determine the levels of MDM2, p53 and MDM2-p53 complex in Clone 6 cells grown at 32° C. for 24 hours (A) or continuously at 37° C. (B).

FIGS. 3A–3C are graphs showing the results of binding MDM2 to a peptide library as determined by ELISA assay using monoclonal antibody 4B2. The library of human and mouse p53 had been challenged with insect cell extract alone (SF9) and insect cell extract expressing mouse MDM2 (SF9 Mus MDM2. The results of peptides numbers 3–50 of the N-terminal to mid region of human p53 are shown in 3A, and the remainder of the human p53 amino acid sequence and the N-terminal sequence of mouse p53 in 3B. 3C shows the results from a control experiment using certain peptides from B in order to verify the specificity of the detecting antibody 4B2.

FIG. 4 identifies the peptide sequences to which MDM2 bound (SEQ ID NOS:1, 20–22), and defines the consensus binding site on human and mouse p53. (SEQ ID NOS:11, 12).

FIG. 6 shows the level of binding between MDM2 and a series of peptides based upon the sequence of amino acids 18–23 of p53 (SEQ ID NOS:11, 23–50).

FIG. 7 illustrates an immunoassay procedure of the invention.

DETAILED DESCRIPTION OF THE INVENTION

Figure 1B:
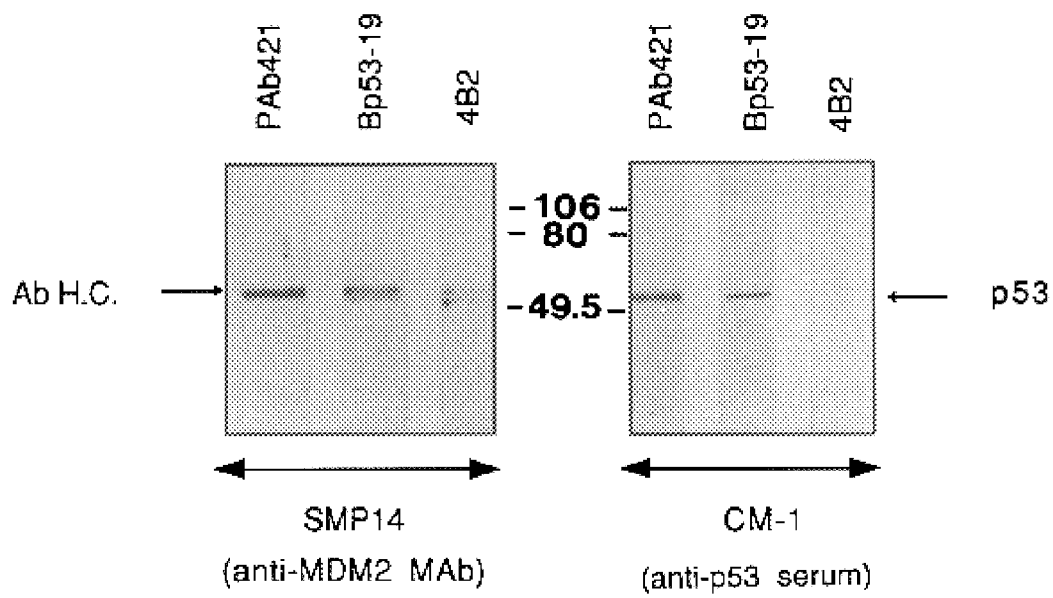

The first indication of an interaction between MDM2 protein and p53 protein emerged from work on a rat cell line, Clone 6, which expressed a temperature sensitive mutant form of mouse p53 (Barak and Oren, 1992; Michalovitz, D., et al. (1990). Cell, 62, 671–680; Momand, J., et al. (1992). Cell, 69, 1237–1245). MDM2 was readily observed to form a complex at 32° C. with p53 but was just detectable when cells were grown at 37° C.

The formation of a p53-MDM2 complex in Clone 6 cells at 32° C. and 37° C. was re-examined in a quantitative manner. The results confirm previous immunoprecipitation observations that the level of MDM2 at the lower temperature is significantly elevated, approximately 10–30 fold greater than that at 37° C., at which temperature MDM2 is only just detectable. Consequently, the p53-MDM2 complex is readily observed at 32° C. and not at 37° C. The levels of p53 also vary at the two different temperatures. However, the p53 levels are elevated approximately five fold at 37° C. as compared with that at 32° C., —the opposite behaviour to that of MDM2. Accordingly, the difference in the levels of p53 and MDM2 are likely to have alternative explanations. In the case of MDM2 other groups have established that the increase of MDM2 at 32° C. is due to increased transcription of MDM2 due to a conformational change in p53 to a presumed transcriptional active form (Barak, Y., et al. (1993).

Embo J., 12, 461–468; Wu, X., et al. (1993). Genes Dev., 7, 1126–1132). The same explanation does not apply for p53 even though wild type p53 is required for p53 expression (Deffie, A., et al. G. (1993). Mol. Cell. Biol., 13, 3415–3423), and is probably explained by the increased half life of the mutant conformation of p53 at 37° C. (Gannon J. V. et al (1991) Nature, 349, 802–806). Data described herein after using both direct observation of the p53-MDM2 complex by ELISA and immunoprecipitation combined with the indirect inference of the loss of the Bp53-19 epitope suggested that nearly all p53 molecules are complexed to excess MDM2 protein in C6 cells at 32° C. This is not consistent with the powerful p53 dependant transcriptional response seen in these cells at this temperature and suggests that either that complexing to MDM2 is unable to completely inactivate p53 in vivo or that small amounts of "free" p53 may be very active. The complex between p53 and MDM2 may be regulated in cells to release functional p53 at the individual cell level perhaps as a cell cycle dependant response.

The present invention is based upon the identification of the minimal MDM2 binding site to be TFSD/GLW (SEQ ID NOS:11, 23–50). This site is in a location broadly reported by other groups to be the MDM2 binding domain of p53, specifically aa1–41 and 13–57 (Oliner, J. D., et al. (1993). Nature, 362, 857–860), aa1–52 (Chen, J., et al. (1993). Mol Cell Biol, 13, 4107–14) and aa1–59 (Brown, D. R., et al. (1993). Mol. Cell. Biol., 13, 6849–57.) Notably, a construct generated by Oliner and co-workers encompassing aa13–41 of p53 was not sufficient for MDM2 binding in a three hybrid protein system, and differs from our observations. The disparity might be explained by the close proximity of the fusion protein sequence adjacent to the TFSDGLW sequence at aa18–23 as the present data does show that flanking sequences do contribute in a minor way to MDM2 binding. The TFSD/GLW sequence is very closely adjacent to the transactivation domain aa20–42 (Unger, T., et al. (1992). Embo J., 11, 1383–1390), and as shown by others the binding of MDM2 to this site interferes with the transcriptional activity of p53 (Oliner, J. D., et al. (1993). Nature, 362, 857–860). While substitution analysis of the MDM2 binding site on p53 identified the TFSD/GLW sequence (SEQ ID NOS:2, 3, and 7) to be the key region required for MDM2 to bind p53, other residues flanking this site also contribute in a minor way to MDM2 binding, but clearly the TFSD/GLW sequence (SEQ ID NOS:2, 3, and 7) is a minimal target for agents that might disrupt complex formation without effecting the transactivation activity (for which as yet the key residues are undetermined). The first two residues TF are part of the conserved box I, and the latter four SD/GLW (SEQ ID NOS:8, 9) are outside but are also part of a region of p53 that is conserved from Xenopus to man.

The corresponding binding site on MDM2 for p53 has variously been reported to be between aa1–121, 19–102 (Chen, J., et al. (1993). Mol. Cell. Biol., 13, 4107–14) together with aa102–294 or 249–491, and also 1–221 (Brown, D. R., et al. (1993). Mol. Cell. Biol., 13, 6849–57). Notably, a monoclonal antibody against the N-terminal region of human MDM2, 3G5 (maps at aa59–89) is able to immunoprecipitate MDM2 but not co-immunoprecipitate p53 (Chen, J., et al. (1993). Mol Cell Biol, 13, 4107–14), an analogous observation to our findings with antibody Bp53–19.

The binding of MDM2 to p53 peptides has obvious parallels to a similar study that used small peptides to identify the binding sites of Adenovirus E1A and human papilloma virus E7 for a range of proteins including retinoblastoma protein, p107, cyclin A and p130 (Dyson, N., et al. (1992a). J. Virol., 66, 4606–4611). The MDM2 binding site on p53, appears to be a single domain rather than two domains as in the case of E1A and E7. The MDM2 binding site on p53 overlaps precisely with a highly immunogenic epitope on the protein; many independently isolated monoclonal antibodies to p53 recognise the site, and antibodies to it are present in the sera of cancer patients (Schlichtholtz, B., et al. (1993). Cancer Res., 52, 6380–6384). This suggests that it has an exposed and defined structure. It is possible that the amino acid sequence of the complementarity determining regions of these antibodies will show homology to the p53 binding site of MDM2. It also suggests that anti-p53 antibodies used to examine p53 levels where high levels of MDM2 are present must be chosen with care. Binding of MDM2 to this site may be regulated by phosphorylation since there is a DNA-dependent kinase site at serine 20 (Less-Miller, S. P. et al. (1990). Mol. Cell. Biol., 10, 6472–6481) and other phosphorylation sites at serine 6, 9 and 15 (Samad, A., et al. (1986). Proc. Natl. Acad. Sci. U.S.A., 83, 897–901; Meek, D.W. et al. (1988). Mol. Cell. Biol., 8, 461–465; Meek and Eckhardt, 1988).

The following examples are provided to exemplify various aspects of the invention and are not intended to limit the scope of the invention.

In these examples, the following materials and methods were used.

Materials and Methods

Cell Culture

Clone 6 cells (Michalovitz et al., 1990) were grown in Dulbecco's Modified Eagle Medium (DMEM) supplemented with 10% FCS at either 32 or 37° C. The Spodoptera frugiperda cell line, SF9, was grown at 27° C. in ExCell 400 medium (J. R. H. Biosciences, Sera-Lab, UK) supplemented with 5% FCS and glutamine.

Expression of MDM2 in Insect Cells

The mouse mdm2 gene was obtained from a mouse prostate cell line (Lu et al., 1992) by polymerase chain reaction and then cloned into a Spododoptera frugiperda expression vector pVL1393 using standard DNA and baculovirus expression techniques. An expression clone was identified by the production of a 90–95kDa protein that was recognized by anti-MDM2 antibodies.

Antibodies p53 protein was detected using the polyclonal sera CM1 (Midgley, C. A., et al. (1992). J. Cell. Sci., 101, 183–189), or monoclonal antibodies PAb421 (Harlow E et al., (1981) J. Virol., 39, 861–869) and Bp53-19 (Bartek J., et al (1993). J. Pathol., 169, 27–34). MDM2 was detected using rabbit anti-MDM2 polyclonal sera (Barak, Y., et al. (1993). Embo J., 12, 461–468) or monoclonal antibody 4B2 (Chen et al., 1993) and SMP14 (a previously unreported monoclonal antibody raised by us against a peptide, CSRPSTSSR-RRAISE (SEQ ID NO:10), containing part of the human MDM2 sequence from aa154 to 167 (Oliner, J. D., et al. (1992). Nature, 358, 80–83) the first cysteine is not part of the MDM2 sequence but was added to provide an extra coupling option). An antibody, PAb419, raised against SV40 large T antigen (Harlow, E., et al. (1981). J. Virol., 39, 861–869) was used as an irrelevant control for immunoprecipitations.

Immunoprecipitation

Cells were lysed in ice-cold NET buffer (50 mM Tris-HCl, pH8.0, 150 mM NaCl, 5 mM EDTA, 1% NP40) containing 1 mM phenylmethylsulphonyl fluoride, for 30 min at 4° C. Debris was removed from the cell extract by centrifugation at 14,000 rpm in a refridgerated Eppendorf centrifuge. The immunoprecipitation procedure was essentially as previously described (Gannon, J. V., et al. (1990). Embo J., 9, 1595–1602) using 1 $\mu$g of purified mouse monoclonal antibody, and Protein G Sepharose beads (Pharmacia) for both pre-absorption of the cell extracts and subsequent isolation of the antibody-protein complex.

Screening of p53 Peptide Library

Peptide libraries of the entire human p53 protein and a partial N-terminal region of the mouse p53 protein was obtained from Chiron Mimotopes P/L (Victoria, Australia).

The libraries were in the form of 15 mer peptides linked to biotin via an additional peptide spacer region of serine-glycine-serine-glycine, and each peptide shared a 5 amino acid overlap with the previous peptide in the primary sequence. ELISA plates were coated with 100 $\mu$l of 5 $\mu$g/ml streptavidin (vector labs) per well and incubated overnight at 37° C. and then blocked with phosphate buffered saline (PBS) containing 2% bovine serum albumin (BSA) for 1 hour at room temperature. The stock biotinylated peptides were diluted to 5 $\mu$g/ml in PBS containing 0.1 BSA and 50 $\mu$l of each were plated into designed wells and then incubated at room temperature for 1 hour. The plates were washed four times with PBS containing 0.1% Tween 20 before addition of the cell extract (50 $\mu$l of 1–4 mg/ml per well) or purified protein. The plates were incubated at 4° C. for 2–3 hours, before washing four times with PBS containing 0.1% Tween 20 to remove unbound protein. In the case of cell extracts bound protein was detected with the appropriate primary antibody at 1–3 $\mu$g/ml, and followed by an anti-mouse horse radish peroxidase conjugate and 3'3'4'4'-tetramethyl benzidine (TMB) substrate as in the standard ELISA assay (Harlow, E., et al (1988). Antibodies: a laboratory manual. New York. Cold Spring Harbor Laboratory Press and Lane, 1988).

The levels of p53, MDM2, and complexes thereof were determined by a two site immunoassay using stated antibodies. Mouse monoclonal antibodies were used as the solid phase by incubating Falcon microtitre dish wells with 50 $\mu$l of a 30 $\mu$g/ml solution of purified antibody overnight at 4° C. The plates were blocked with 2% bovine serum albumin in PBS for 2 h at room temperature, and washed with PBS. Cell extracts were prepared as described for immunoprecipitations and then serially two-fold diluted before adding 50 $\mu$l per well and incubating at 4° C. for two hours. The plates were then washed with 0.1% NP-40 in PBS, before addition of 50 $\mu$l of detecting polyclonal antisera at $\frac{1}{1000}$ dilution. The plates were washed again with 0.1% NP-40 in PBS and 50 $\mu$l of $\frac{1}{1000}$ dilution peroxidase conjugated swine anti-rabbit Ig serum (DAKO) was added for 2 h, then visualised by the TMB reaction.

EXAMPLES

Example 1

Immunoprecipitation of MDM2, p53 and the MDM2-p53 Complex

The observation that the rat cell line, Clone 6 expressed a temperature sensitive mutant form of mouse p53 was reexamined using a panel of p53 monoclonal antibodies.

Western blots were obtained of immunoprecipitates of MDM2, p53 and the MDM2-p53 complex from Clone 6 cells grown at 32° C. for 24 hrs (FIG. 1A) or continuously at 37° C. (FIG. 1B). The immunoprecipitates were obtained using 1 g of purified antibody which were as follows: in lanes 1 and 4,—PAb421; in lanes 2 and 5,—Bp53-19; and in lanes 3 and 6,—4B2. MDM2 was detected in lanes 1, 2 and 3 using SMP14 antibody supernatant and rabbit anti-mouse horse radish peroxidase conjugate; and p53 detected in lanes 4, 5 and 6 using a 1 in 200 dilution of DM-1 and swine anti-rabbit horse radish peroxidase conjugate. An irrelevant antibody, PAb419, did not immunopecipitate either MDM2 or p53 from cell extracts prepared at either 32° C. or 37° C. (data not shown). The molecular weight of the markers are given in kDa.

It was surprisingly found that one of the antibodies, Bp53-19, failed to immunoprecipitate p53 from Clone C6 cells grown at 32° C. for 24 hours , but efficiently precipitated p53 from cells grown continuously at 37° C. (compare FIG. 1A track 5 with FIG. 1B track 5), whereas PAb421 precipitated p53 at both temperatures (FIG. 1A track 4 and 1B track 4). Investigations were then carried out to determine whether Bp53-19 would co-immunoprecipitate MDM2 with p53. From the immunoprecipitation western data in FIG. 1A and 1B it is clear that Bp53-19 does not co-immunoprecipitate MDM2 from cell extracts grown at 32 or 37° C. (track 2 in FIG. 1A and B). Other p53 antibodies such as PAb421 do however co-immunoprecipitate MDM2 with p53 at 32° C. but not at 37° C. (track 1 FIGS. 1A and B). Conversely, antibodies against MDM2 such as 4B2, FIG. 1, and SMP14 (data not shown) co-immunoprecipitate p53 at 32° C. but not at 37° C. (track 6 FIGS. 1A and B). The two bands recognized by 4B2 (and SMP14) at just below 80 kDa are truncated forms of rat MDM2, as full length migrates on an SDS-PAGE gel with an apparent relative molecular mass of 90 kDa, multiple forms of MDM2 are often observed (Chen, J., et al. (1993). Mol Cell Biol, 13, 4107–14).

Example 2

Two-site Immunoassay to Determine Levels of MDM2, p53 and MDM2-p53 Complex

Two-site immunoassays were carried out to determine the levels of MDM2, p53 and MDM2-pS3 complex in Clone 6 cells grown at 32° C. for 24 hrs (FIG. 2A) or continuously at 37° C. (FIG. 2B). In FIG. 2A the coating antibodies were one of the following purified antibodies as stated in the figure legends: 4B2, 421 and Bp53-19, probed with rabbit anti-p53 serum CM1 or rabbit anti-MDM2 serum, and then detected using swine anti-rabbit horse radish peroxidase conjugate and TMB as substrate. At 37° C. the MDM2-p53 complex was undetectable by any combination of antibodies.

The two-site immunoassays of the levels of MDM2, p53 and MDM2-p53 complex at 32° C. and 37° C. are consistent with the immunoprecipitation results of Example 1. A striking feature apparent from the data in FIG. 2A is that the levels of p53 and p53-MDM2 complex are very similar suggesting that most, but not all, p53 is in complex with MDM2 at 32° C. The inability of BpS3-19 to detect a p53-MDM2 complex at 32° C. is again notable since other combinations of antibodies are able to do so.

From comparison of the two-site immunoassays at 32° C. and 37° C. it is clear why MDM2 is not immunoprecipitated at 37° C., as the levels of MDM2 protein are very much lower and are only just detectable. No MDM2-p53 complex could be detected by the two-site immunoassay of cell extracts prepared at 37° C., see FIG. 2B, where the data for the 4B2 (as the capture antibody) and CM1 (as the detecting antibody) combination of antibodies is shown (similarly antibodies PAb421 or Bp53-19 and rabbit anti-MDM2 polyclonal did not detect the complex). The diminished level of MDM2 at 37° C., less than 10% of that at 32° C., is in contrast to the situation with p53 which is elevated approximately 5 fold relative to the levels at 32° C.

The explanation for the ability of PAb421 and 4B2 only being able to coprecipitate p53 and MDM2 together at 32° C., but not at 37° C. is consistent with difference in levels of MDM2 at the two temperatures, and also with the published observations that mdm2 expression is dependent on the "wild-type" form of p53 predominantly present at 32° C.

The failure of Bp53-19 to co-immunoprecipitate MDM2 or detect the p53-MDM2 complex at 32° C. is unexpected for two reasons. Firstly, the two-site assay suggests there is MDM2 protein in excess, which is able to form complexes with p53 as detected by the capturing antibodies PAb421 and 4B2. Secondly, the two-site immunoassay at 37° C. suggests that Bp53-19 is almost as efficient as PAb421 at recognizing p53 in the cell extracts. The simplest interpretation for this observation is that BpS3-19 recognizes the same region on p53 that MDM2 binds to.

Example 3

Identification of MDM2-p53 Binding Site

It has previously been shown that Bp53-19 and MDM2 interact with the amino acid terminal end of p53 (Stephen et al manuscript in preparation; Oliner, J. D., et al. (1993). Nature, 362, 857–860). A complete peptide library of the human p53 protein, and a partial peptide library of the mouse p53 protein were available to identify the region to which MDM2 binds. The human p53 sequence starts at peptide number 3 and ends at peptide 79, and each peptide consists of 15 amino acids, with the last five amino acids being present in the next peptide along. The mouse p53 sequence is partial and consists of the N-terminal sequence from amino acid 1–92, again each overlapping the next and previous peptide by five amino acids.

Figure 3B:
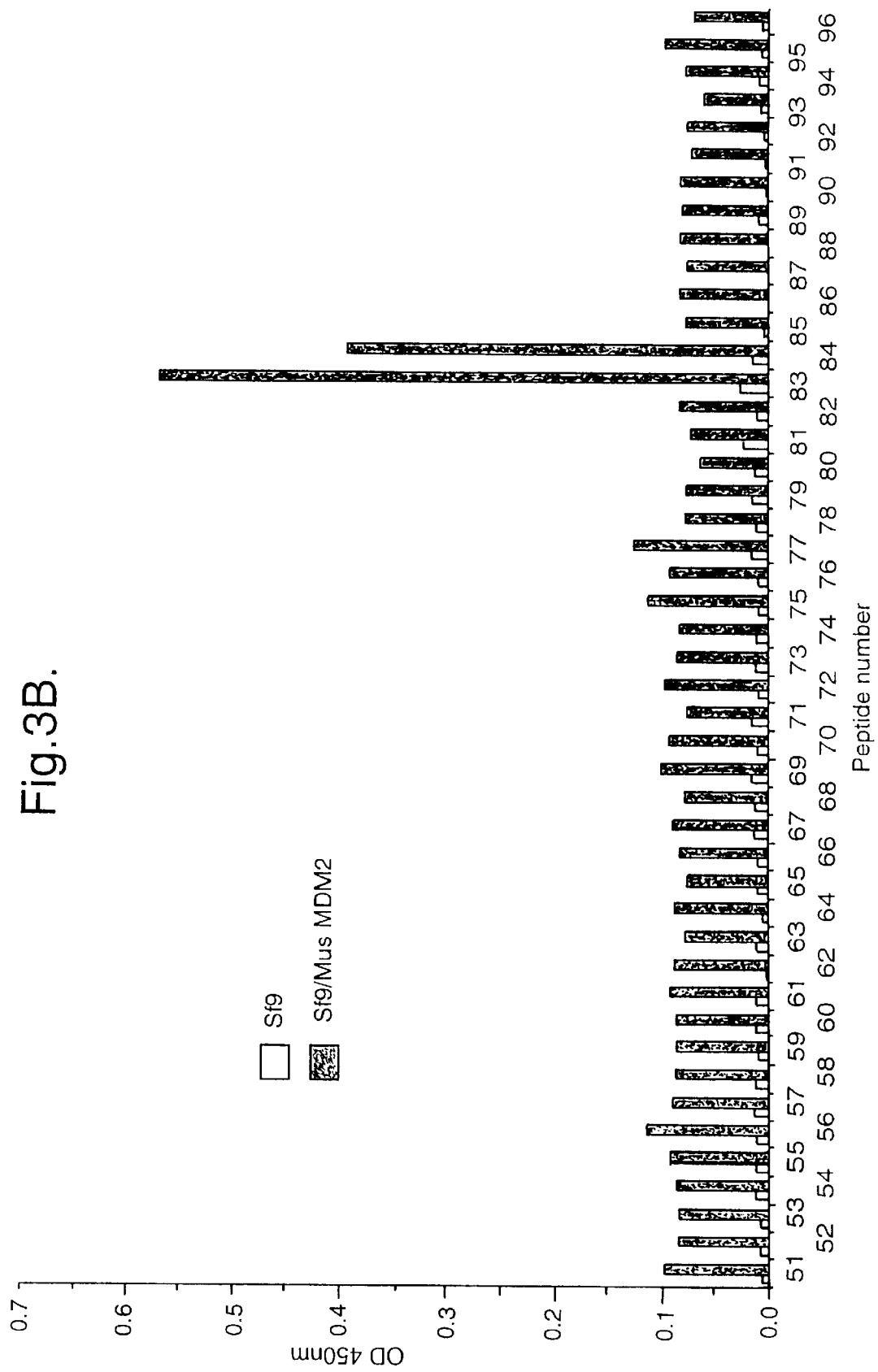
Figures 3C, 4:
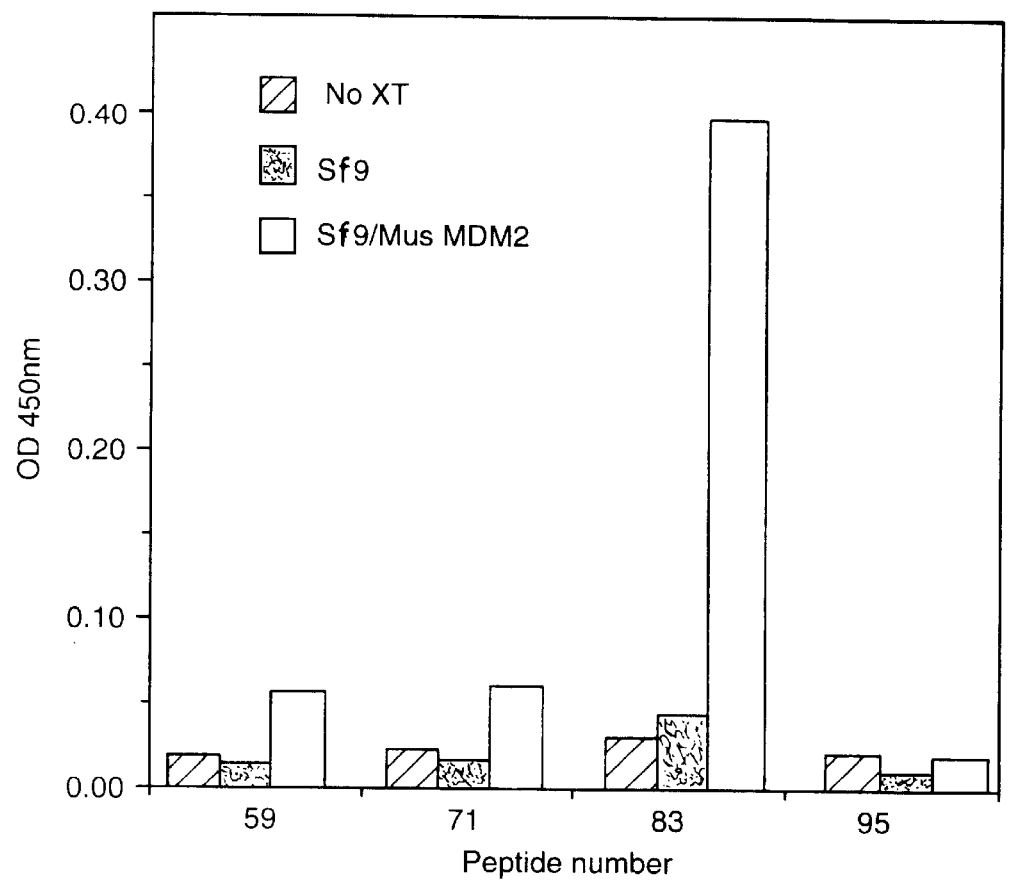

These libraries consisted of 15 amino acid long sections of the p53 primary amino acid sequence, that consecutively overlapped by 5 amino acids, and were each attached to biotin via a 4 amino acid long spacer. By immobilizing the biotinylated peptides on streptavidin coated ELISA plates the MDM2 binding site on p53 could be quickly identified if it was encompassed within a stretch of fifteen amino acids or less. Extract containing MDM2 was added to an ELISA plate with the peptide library bound to it, and the bound MDM2 protein was later detected using monoclonal antibody 4B2 and the standard ELISA assay. Several sources of recombinant MDM2 protein were used to challenge the p53 library, these included crude extracts and partially purified preparations of human and mouse MDM2 expressed in *E.coli* and also mouse MDM2 expressed in insect cells; —all forms identified the same peptides in the p53 library. The results using the mouse MDM2 expressed in insect cells are shown in FIGS. 3A and B. The peptide library was challenged with insect cell extract alone, SF9, and insect cell extract expressing mouse MDM2, SF9 Mus MDM2. Binding of MDM2 to the peptides was determined by an ELISA assay using monoclonal antibody 4B2, and then detecting bound antibody with rabbit anti-mouse Ig conjugated horse radish peroxidase and TMB substrate. In FIG. 3C is shown the results from a control experiment using peptides 59, 71, 83 and 95, as used in FIG. 3B but conducted in the presence or absence of extract to verify the specificity of the detecting antibody, 4B2. The results are presented alongside the ELISA readings for extract of insect cells alone not expressing mouse MDM2. The specificity is remarkable, —suggesting a strong interaction between MDM2 and p53 derived peptides. From the controls shown in FIG. 3C it can be seen that the binding is only observed in the presence of extract expressing MDM2, and is not due to the antibody recognizing the peptide alone, moreover identical results were obtained using SMP14 as the primary detecting antibody (data not shown).

The four peptides that bind MDM2 are shown in FIG. 4. Peptides 5 and 6 identify a site at the N-terminal end of human p53, whereas peptides 83 and 84 identify the corresponding region in the N-terminal end of mouse p53. Collectively, these four peptides define the consensus MDM2 binding site on p53 to be —QETFSD/GLWKL (SEQ ID NOS:11, 12), the aspartate to glycine being the only amino acid difference between the human and mouse sequence. The peptides involved in binding MDM2 are also those recognized by the p53 antibodies DO-1 and Bp53-19 (Stephen et al, manuscript in preparation).

Figure 5C:
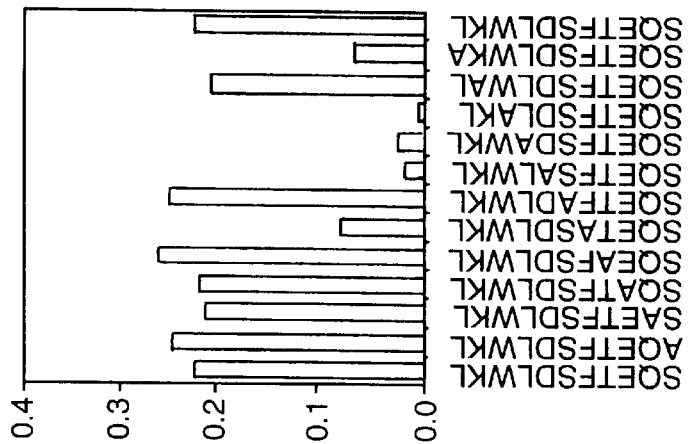
FIGS. 5A–5C show the key residues required for binding MDM2, antibody DO-1 and antibody Bp53–19 respectively (SEQ ID NOS:17, 22–33).
Figure 5B:
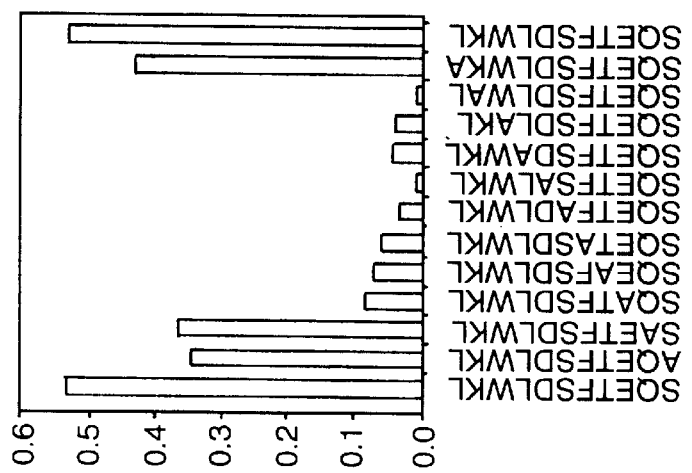
Figure 5A:
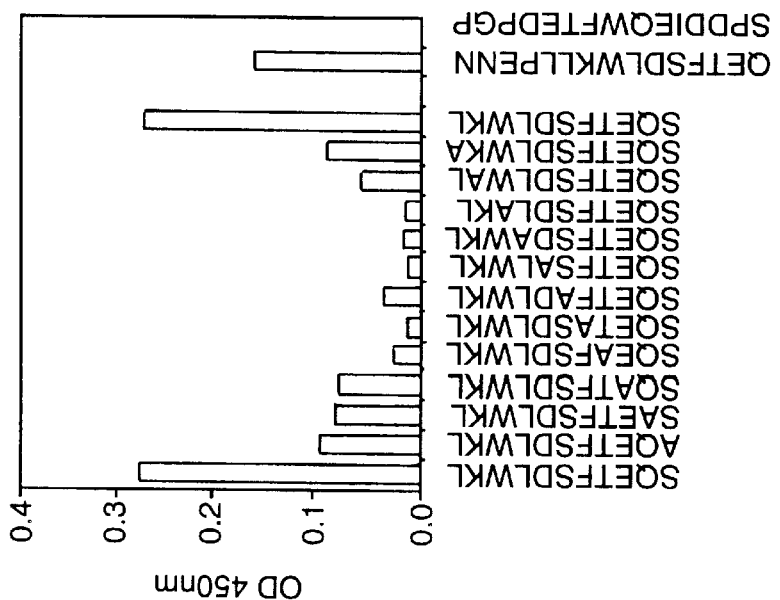

To define key residues on p53 that are involved in the interaction with MDM2 a form of the consensus binding site sequence -QETFSDLWKL (SEQ ID NO:11)- was modified by substituting alanine at each position in the sequence and determining what effect this had on the binding of MDM2 from the insect cell extract expressing MDM2. This experiment was conducted in concert with examining the effect on binding of the antibodies DO-1 and Bp53-19. The results are presented in FIG. 5. The amino acid sequences are as stated. In A the sequence QETFSDLWKLLPENN (SEQ ID NO:1) represents the sequence of peptide 6 from FIG. 3 and SPDDIEQWFTEDPGP (SEQ ID NO:13) is an irrelevant peptide control. Formally the first serine residue on the stated peptide is part of the spacer coupling the consensus peptide to biotin, since serin also precedes the consensus p53 sequence this residue was also substituted with alanine. With regard to MDM2 binding all alanine substitutions in the consensus binding site reduce the level of binding as measured by ELISA, however, the key residues would appear to be TFSDLW (SEQ ID NO:2) as substitutions in these positions reduce the amount of MDM2 binding to less than 15% of that seen with the unchanged consensus sequence. Interestingly, a higher level of binding of MDM2 is observed to the smaller consensus peptide rather than to peptide 6 (QETFSDLWKLLPENN) (SEQ ID NO:7) of the p53 peptide library reaffirming the definition of the binding site. In the case of monoclonal antibody DO-1 binding to the consensus sequence the key residues are ETFSDLK (SEQ ID NO:14), with D and K being the most crucial. The importance of the aspartate residue to the DO-1 epitope is consistent with the report that DO-1 only recognizes human p53 and not mouse p53,—the only difference being an aspartate to glycine change. While this difference has a critical affect on DO-1 binding it does not grossly affect the interaction of MDM2 Δ with the protein or peptides. However substitution of alanine for aspartate at this position blocks binding of all three protein ligands. The ability of MDM2 to distinguish alanine from either glycine or aspartate at this position may imply that the polar environment of this region of the binding site is critical for the interaction. It has also been established from phage display libraries that the epitope of DO-1 is FSDLWKL (SEQ ID NO:15) (Stephen et al, manuscript in preparation), which is in agreement with our observations on key residues. For the antibody Bp53-19 the alanine substitution series identifies the key residues to be F-DLW (SEQ ID NOS:16)- with the latter three residues being the most crucial, and is similar to the requirements for MDM2 binding to the consensus binding site. Not surprisingly, it was found that the pre-binding of antibody Bp53-19 onto he SQETFSDLWKL (SEQ ID NO:17) biotinylated peptide blocked binding of MDM2 to the peptide when added later (data not shown).

Example 4

Further Characterisation of the p53-MDM2 Binding Site

The process of Example 3 was repeated but using insect cells infected with baculovirus expressing Mus MDM2 from SF9 cells in two 180ml$^2$ tissue culture flasks. The extract was prepared in approximately three mils of lysisi buffer to give a concentrated supernatant of 13 mg/ml.

As before, the MDM2 binding site was defined by alanine substitution of the p53 derived peptide, SQETFSDLWL (SEQ ID NO:18) and the results are shown in FIG. 6. Additionally other conserved substitutions were tested (i.e those commonly seen in highly conserved proteins of identical function) and the results are also shown in FIG. 6. With a higher protein concentration, (13 mg/ml as opposed to 1–4 mg/ml) the alanine substitution experiment reveals the same six amino acids are important ($^{18}$TFSDLW$^{23}$) (SEQ ID NO:2) in addition to glutamate (ETFSDLW) (SEQ ID NO:18). This data however establishes that the most critical residues are F–LW as these are intolerant of both alanine substitutions and some, if not all of the conserved substitutions.

A further interesting observation relates to the fact that substitution of the aspartate residue for the glutamate enhances binding of MDM2, indicating that such a residue may usefully be included in the therapeutic peptides of the invention. This also illustrates that this approach can lead to the discovery of agents that have enhanced binding to MDM2.

Additional References

Dyson, N., et al. (1992b). J. Virol., 66, 6893–6902.
Houghten, R. A., et al. (1991). Nature, 354, 84–86. Lu, X., et al (1992). Cell, 70, 153–161.

What is claimed is:

1. A method for interfering with the binding of p53 to an oncogene protein or a fragment thereof that binds to p53, said method comprising:

contacting said p53 and said oncogene protein or fragment thereof with a compound comprising (a) a peptide fragment not exceeding 28 amino acids of p53 protein which includes at least the sequence FxxLW (SEQ ID NO:4), wherein x is any amino acid, (b) a peptide analogue of the peptide fragment of (a) which comprises the sequence FxxLW (SEQ ID NO:4) or (c) an organic molecule that is modeled to resemble the three-dimensional structure of the amino acid residues FxxLW (SEQ ID NO: 4) as they appear at amino acid residues 19–23 in human p53, in an amount effective to interfere with the binding of said p53 to said oncogene protein or fragment thereof;

wherein (a), (b) or (c) binds to said oncogene protein or fragment thereof and thereby interferes with its binding to said p53.

2. The method according to claim 1, wherein (a) is a peptide fragment of from 5 to 10 amino acids.

3. The method according to claim 1, wherein (a) is a peptide fragment of from 12 to 28 amino acids.

4. The method according to claim 1, wherein (a) comprises the sequence FXELW (SEQ ID NO:5), where x is any amino acid.

5. The method according to claim 1, wherein (a) comprises the sequence TFSDLW (SEQ ID NO:2) or TFSGLW (SEQ ID NO:3).

6. The method according to claim 1, wherein (a) comprises the sequence QETFSDLWKLLPENN (SEQ ID NO:1).

7. The method according to claim 1, wherein (a) comprises the sequence EPPLSQETFSDLWKL (SEQ ID NO:11).

8. The method according to claim 1, wherein said compound comprises a peptide analogue of the peptide fragment of (a) which comprises the sequence FxxLW (SEQ ID NO:4).

9. The method according to claim 1, wherein said compound comprises an organic molecule that is modeled to resemble the three-dimensional structure of the amino acid residues FxxLW as they appear at amino acid residues 19–23 in human p53.

10. The method according to claim 1, wherein said oncogene protein is MDM2.

11. The method according to claim 10, wherein said MDM2 is human MDM2.

12. The method according to claim 1, wherein said step of contacting occurs in vitro.

* * * * *

SEQUENCE LISTING (1) GENERAL INFORMATION:

(iii) NUMBER OF SEQUENCES: 50

(2) INFORMATION FOR SEQ ID NO:1:

(i) SEQUENCE CHARACTERISTICS:
        (A) LENGTH: 15 amino acids
        (B) TYPE: amino acid
        (C) STRANDEDNESS:
        (D) TOPOLOGY: unknown (xi) SEQUENCE DESCRIPTION: SEQ ID NO:1:

Gln Glu Thr Phe Ser Asp Leu Trp Lys Leu Leu Pro Glu Asn Asn
1               5                   10                  15

(2) INFORMATION FOR SEQ ID NO:2:

(i) SEQUENCE CHARACTERISTICS:
        (A) LENGTH: 6 amino acids
        (B) TYPE: amino acid
        (C) STRANDEDNESS:
        (D) TOPOLOGY: unknown (xi) SEQUENCE DESCRIPTION: SEQ ID NO:2:

Thr Phe Ser Asp Leu Trp
1               5

(2) INFORMATION FOR SEQ ID NO:3:

(i) SEQUENCE CHARACTERISTICS:
        (A) LENGTH: 6 amino acids
        (B) TYPE: amino acid
        (C) STRANDEDNESS:
        (D) TOPOLOGY: unknown (xi) SEQUENCE DESCRIPTION: SEQ ID NO:3:

Thr Phe Ser Gly Leu Trp
1               5

(2) INFORMATION FOR SEQ ID NO:4:

(i) SEQUENCE CHARACTERISTICS:
        (A) LENGTH: 5 amino acids
        (B) TYPE: amino acid
        (C) STRANDEDNESS:
        (D) TOPOLOGY: unknown (xi) SEQUENCE DESCRIPTION: SEQ ID NO:4:

Phe Xaa Xaa Leu Trp
1               5

(2) INFORMATION FOR SEQ ID NO:5:

(i) SEQUENCE CHARACTERISTICS:
        (A) LENGTH: 5 amino acids
        (B) TYPE: amino acid
        (C) STRANDEDNESS:
        (D) TOPOLOGY: unknown (xi) SEQUENCE DESCRIPTION: SEQ ID NO:5:

Phe Xaa Glu Leu Trp
1               5

(2) INFORMATION FOR SEQ ID NO:6:

(i) SEQUENCE CHARACTERISTICS:
            (A) LENGTH: 6 amino acids
            (B) TYPE: amino acid
            (C) STRANDEDNESS:
            (D) TOPOLOGY: unknown (xi) SEQUENCE DESCRIPTION: SEQ ID NO:6:

Thr Phe Ser Glu Leu Trp
1               5

(2) INFORMATION FOR SEQ ID NO:7:

(i) SEQUENCE CHARACTERISTICS:
            (A) LENGTH: 7 amino acids
            (B) TYPE: amino acid
            (C) STRANDEDNESS:
            (D) TOPOLOGY: unknown (xi) SEQUENCE DESCRIPTION: SEQ ID NO:7:

Thr Phe Ser Asp Gly Leu Trp
1               5

(2) INFORMATION FOR SEQ ID NO:8:

(i) SEQUENCE CHARACTERISTICS:
            (A) LENGTH: 4 amino acids
            (B) TYPE: amino acid
            (C) STRANDEDNESS:
            (D) TOPOLOGY: unknown (xi) SEQUENCE DESCRIPTION: SEQ ID NO:8:

Ser Asp Leu Trp
1

(2) INFORMATION FOR SEQ ID NO:9:

(i) SEQUENCE CHARACTERISTICS:
            (A) LENGTH: 4 amino acids
            (B) TYPE: amino acid
            (C) STRANDEDNESS:
            (D) TOPOLOGY: unknown (xi) SEQUENCE DESCRIPTION: SEQ ID NO:9:

Ser Gly Leu Trp
1

(2) INFORMATION FOR SEQ ID NO:10:

(i) SEQUENCE CHARACTERISTICS:
            (A) LENGTH: 15 amino acids
            (B) TYPE: amino acid
            (C) STRANDEDNESS:
            (D) TOPOLOGY: unknown (xi) SEQUENCE DESCRIPTION: SEQ ID NO:10:

Cys Ser Arg Pro Ser Thr Ser Ser Arg Arg Ala Ile Ser Glu
1               5                   10                  15

(2) INFORMATION FOR SEQ ID NO:11:

(i) SEQUENCE CHARACTERISTICS:
            (A) LENGTH: 10 amino acids
            (B) TYPE: amino acid
            (C) STRANDEDNESS:
            (D) TOPOLOGY: unknown (xi) SEQUENCE DESCRIPTION: SEQ ID NO:11:

```
Gln Glu Thr Phe Ser Asp Leu Trp Lys Leu
1               5                   10

(2) INFORMATION FOR SEQ ID NO:12:

(i) SEQUENCE CHARACTERISTICS:
        (A) LENGTH: 10 amino acids
        (B) TYPE: amino acid
        (C) STRANDEDNESS:
        (D) TOPOLOGY: unknown (xi) SEQUENCE DESCRIPTION: SEQ ID NO:12:

Gln Glu Thr Phe Ser Gly Leu Trp Lys Leu
1               5                   10

(2) INFORMATION FOR SEQ ID NO:13:

(i) SEQUENCE CHARACTERISTICS:
        (A) LENGTH: 15 amino acids
        (B) TYPE: amino acid
        (C) STRANDEDNESS:
        (D) TOPOLOGY: unknown (xi) SEQUENCE DESCRIPTION: SEQ ID NO:13:

Ser Pro Asp Asp Ile Glu Gln Trp Phe Thr Glu Asp Pro Gly Pro
1               5                   10                  15

(2) INFORMATION FOR SEQ ID NO:14:

(i) SEQUENCE CHARACTERISTICS:
        (A) LENGTH: 7 amino acids
        (B) TYPE: amino acid
        (C) STRANDEDNESS:
        (D) TOPOLOGY: unknown (xi) SEQUENCE DESCRIPTION: SEQ ID NO:14:

Glu Thr Phe Ser Asp Leu Lys
1               5

(2) INFORMATION FOR SEQ ID NO:15:

(i) SEQUENCE CHARACTERISTICS:
        (A) LENGTH: 7 amino acids
        (B) TYPE: amino acid
        (C) STRANDEDNESS:
        (D) TOPOLOGY: unknown (xi) SEQUENCE DESCRIPTION: SEQ ID NO:15:

Phe Ser Asp Leu Trp Lys Leu
1               5

(2) INFORMATION FOR SEQ ID NO:16:

(i) SEQUENCE CHARACTERISTICS:
        (A) LENGTH: 6 amino acids
        (B) TYPE: amino acid
        (C) STRANDEDNESS:
        (D) TOPOLOGY: unknown (xi) SEQUENCE DESCRIPTION: SEQ ID NO:16:

Phe Xaa Asp Leu Trp Xaa
1               5

(2) INFORMATION FOR SEQ ID NO:17:

(i) SEQUENCE CHARACTERISTICS:
        (A) LENGTH: 11 amino acids
        (B) TYPE: amino acid
```

(C) STRANDEDNESS:
            (D) TOPOLOGY: unknown (xi) SEQUENCE DESCRIPTION: SEQ ID NO:17:

Ser Gln Glu Thr Phe Ser Asp Leu Trp Lys Leu
1               5                   10

(2) INFORMATION FOR SEQ ID NO:18:

(i) SEQUENCE CHARACTERISTICS:
            (A) LENGTH: 10 amino acids
            (B) TYPE: amino acid
            (C) STRANDEDNESS:
            (D) TOPOLOGY: unknown (xi) SEQUENCE DESCRIPTION: SEQ ID NO:18:

Ser Gln Glu Thr Phe Ser Asp Leu Trp Leu
1               5                   10

(2) INFORMATION FOR SEQ ID NO:19:

(i) SEQUENCE CHARACTERISTICS:
            (A) LENGTH: 7 amino acids
            (B) TYPE: amino acid
            (C) STRANDEDNESS:
            (D) TOPOLOGY: unknown (xi) SEQUENCE DESCRIPTION: SEQ ID NO:19:

Glu Thr Phe Ser Asp Leu Trp
1               5

(2) INFORMATION FOR SEQ ID NO:20:

(i) SEQUENCE CHARACTERISTICS:
            (A) LENGTH: 15 amino acids
            (B) TYPE: amino acid
            (C) STRANDEDNESS:
            (D) TOPOLOGY: unknown (xi) SEQUENCE DESCRIPTION: SEQ ID NO:20:

Glu Pro Pro Leu Ser Gln Glu Thr Phe Ser Asp Leu Trp Lys Leu
1               5                   10                  15

(2) INFORMATION FOR SEQ ID NO:21:

(i) SEQUENCE CHARACTERISTICS:
            (A) LENGTH: 15 amino acids
            (B) TYPE: amino acid
            (C) STRANDEDNESS:
            (D) TOPOLOGY: unknown (xi) SEQUENCE DESCRIPTION: SEQ ID NO:21:

Pro Leu Ser Gln Glu Thr Phe Ser Gly Leu Trp Lys Leu Leu Pro
1               5                   10                  15

(2) INFORMATION FOR SEQ ID NO:22:

(i) SEQUENCE CHARACTERISTICS:
            (A) LENGTH: 15 amino acids
            (B) TYPE: amino acid
            (C) STRANDEDNESS:
            (D) TOPOLOGY: unknown (xi) SEQUENCE DESCRIPTION: SEQ ID NO:22:

Thr Phe Ser Gly Leu Trp Lys Leu Leu Pro Pro Glu Asp Ile Leu
1               5                   10                  15

(2) INFORMATION FOR SEQ ID NO:23:

(i) SEQUENCE CHARACTERISTICS:
        (A) LENGTH: 11 amino acids
        (B) TYPE: amino acid
        (C) STRANDEDNESS:
        (D) TOPOLOGY: unknown (xi) SEQUENCE DESCRIPTION: SEQ ID NO:23:

```
Ala Gln Glu Thr Phe Ser Asp Leu Trp Lys Leu
1               5                   10
```

(2) INFORMATION FOR SEQ ID NO:24:

(i) SEQUENCE CHARACTERISTICS:
        (A) LENGTH: 11 amino acids
        (B) TYPE: amino acid
        (C) STRANDEDNESS:
        (D) TOPOLOGY: unknown (xi) SEQUENCE DESCRIPTION: SEQ ID NO:24:

```
Ser Ala Glu Thr Phe Ser Asp Leu Trp Lys Leu
1               5                   10
```

(2) INFORMATION FOR SEQ ID NO:25:

(i) SEQUENCE CHARACTERISTICS:
        (A) LENGTH: 11 amino acids
        (B) TYPE: amino acid
        (C) STRANDEDNESS:
        (D) TOPOLOGY: unknown (xi) SEQUENCE DESCRIPTION: SEQ ID NO:25:

```
Ser Gln Ala Thr Phe Ser Asp Leu Trp Lys Leu
1               5                   10
```

(2) INFORMATION FOR SEQ ID NO:26:

(i) SEQUENCE CHARACTERISTICS:
        (A) LENGTH: 11 amino acids
        (B) TYPE: amino acid
        (C) STRANDEDNESS:
        (D) TOPOLOGY: unknown (xi) SEQUENCE DESCRIPTION: SEQ ID NO:26:

```
Ser Gln Glu Ala Phe Ser Asp Leu Trp Lys Leu
1               5                   10
```

(2) INFORMATION FOR SEQ ID NO:27:

(i) SEQUENCE CHARACTERISTICS:
        (A) LENGTH: 11 amino acids
        (B) TYPE: amino acid
        (C) STRANDEDNESS:
        (D) TOPOLOGY: unknown (xi) SEQUENCE DESCRIPTION: SEQ ID NO:27:

```
Ser Gln Glu Thr Ala Ser Asp Leu Trp Lys Leu
1               5                   10
```

(2) INFORMATION FOR SEQ ID NO:28:

(i) SEQUENCE CHARACTERISTICS:
        (A) LENGTH: 11 amino acids
        (B) TYPE: amino acid
        (C) STRANDEDNESS:
        (D) TOPOLOGY: unknown (xi) SEQUENCE DESCRIPTION: SEQ ID NO:28:

Ser Gln Glu Thr Phe Ala Asp Leu Trp Lys Leu
1               5                  10

(2) INFORMATION FOR SEQ ID NO:29:

(i) SEQUENCE CHARACTERISTICS:
        (A) LENGTH: 11 amino acids
        (B) TYPE: amino acid
        (C) STRANDEDNESS:
        (D) TOPOLOGY: unknown (xi) SEQUENCE DESCRIPTION: SEQ ID NO:29:

Ser Gln Glu Thr Phe Ser Ala Leu Trp Lys Leu
1               5                  10

(2) INFORMATION FOR SEQ ID NO:30:

(i) SEQUENCE CHARACTERISTICS:
        (A) LENGTH: 11 amino acids
        (B) TYPE: amino acid
        (C) STRANDEDNESS:
        (D) TOPOLOGY: unknown (xi) SEQUENCE DESCRIPTION: SEQ ID NO:30:

Ser Gln Glu Thr Phe Ser Asp Ala Trp Lys Leu
1               5                  10

(2) INFORMATION FOR SEQ ID NO:31:

(i) SEQUENCE CHARACTERISTICS:
        (A) LENGTH: 11 amino acids
        (B) TYPE: amino acid
        (C) STRANDEDNESS:
        (D) TOPOLOGY: unknown (xi) SEQUENCE DESCRIPTION: SEQ ID NO:31:

Ser Gln Glu Thr Phe Ser Asp Leu Ala Lys Leu
1               5                  10

(2) INFORMATION FOR SEQ ID NO:32:

(i) SEQUENCE CHARACTERISTICS:
        (A) LENGTH: 11 amino acids
        (B) TYPE: amino acid
        (C) STRANDEDNESS:
        (D) TOPOLOGY: unknown (xi) SEQUENCE DESCRIPTION: SEQ ID NO:32:

Ser Gln Glu Thr Phe Ser Asp Leu Trp Ala Leu
1               5                  10

(2) INFORMATION FOR SEQ ID NO:33:

(i) SEQUENCE CHARACTERISTICS:
        (A) LENGTH: 11 amino acids
        (B) TYPE: amino acid
        (C) STRANDEDNESS:
        (D) TOPOLOGY: unknown (xi) SEQUENCE DESCRIPTION: SEQ ID NO:33:

Ser Gln Glu Thr Phe Ser Asp Leu Trp Lys Ala
1               5                  10

(2) INFORMATION FOR SEQ ID NO:34:

(i) SEQUENCE CHARACTERISTICS:
        (A) LENGTH: 11 amino acids

```
            (B) TYPE: amino acid
            (C) STRANDEDNESS:
            (D) TOPOLOGY: unknown (xi) SEQUENCE DESCRIPTION: SEQ ID NO:34:

Asp Gln Glu Thr Phe Ser Asp Leu Trp Lys Leu
1               5                   10

(2) INFORMATION FOR SEQ ID NO:35:

(i) SEQUENCE CHARACTERISTICS:
            (A) LENGTH: 11 amino acids
            (B) TYPE: amino acid
            (C) STRANDEDNESS:
            (D) TOPOLOGY: unknown (xi) SEQUENCE DESCRIPTION: SEQ ID NO:35:

Ser Gln Glu Thr Phe Asp Asp Leu Trp Lys Leu
1               5                   10

(2) INFORMATION FOR SEQ ID NO:36:

(i) SEQUENCE CHARACTERISTICS:
            (A) LENGTH: 11 amino acids
            (B) TYPE: amino acid
            (C) STRANDEDNESS:
            (D) TOPOLOGY: unknown (xi) SEQUENCE DESCRIPTION: SEQ ID NO:36:

Ser Gln Glu Ser Phe Ser Asp Leu Trp Lys Leu
1               5                   10

(2) INFORMATION FOR SEQ ID NO:37:

(i) SEQUENCE CHARACTERISTICS:
            (A) LENGTH: 11 amino acids
            (B) TYPE: amino acid
            (C) STRANDEDNESS:
            (D) TOPOLOGY: unknown (xi) SEQUENCE DESCRIPTION: SEQ ID NO:37:

Ser Gln Glu Thr Ile Ser Asp Leu Trp Lys Leu
1               5                   10

(2) INFORMATION FOR SEQ ID NO:38:

(i) SEQUENCE CHARACTERISTICS:
            (A) LENGTH: 11 amino acids
            (B) TYPE: amino acid
            (C) STRANDEDNESS:
            (D) TOPOLOGY: unknown (xi) SEQUENCE DESCRIPTION: SEQ ID NO:38:

Ser Gln Glu Thr Leu Ser Asp Leu Trp Lys Leu
1               5                   10

(2) INFORMATION FOR SEQ ID NO:39:

(i) SEQUENCE CHARACTERISTICS:
            (A) LENGTH: 11 amino acids
            (B) TYPE: amino acid
            (C) STRANDEDNESS:
            (D) TOPOLOGY: unknown (xi) SEQUENCE DESCRIPTION: SEQ ID NO:39:

Ser Gln Glu Thr Met Ser Asp Leu Trp Lys Leu
1               5                   10
```

(2) INFORMATION FOR SEQ ID NO:40:

(i) SEQUENCE CHARACTERISTICS:
       (A) LENGTH: 11 amino acids
       (B) TYPE: amino acid
       (C) STRANDEDNESS:
       (D) TOPOLOGY: unknown (xi) SEQUENCE DESCRIPTION: SEQ ID NO:40:

Ser Gln Glu Thr Phe Thr Asp Leu Trp Lys Leu
1               5                   10

(2) INFORMATION FOR SEQ ID NO:41:

(i) SEQUENCE CHARACTERISTICS:
       (A) LENGTH: 11 amino acids
       (B) TYPE: amino acid
       (C) STRANDEDNESS:
       (D) TOPOLOGY: unknown (xi) SEQUENCE DESCRIPTION: SEQ ID NO:41:

Ser Gln Glu Thr Phe Pro Asp Leu Trp Lys Leu
1               5                   10

(2) INFORMATION FOR SEQ ID NO:42:

(i) SEQUENCE CHARACTERISTICS:
       (A) LENGTH: 11 amino acids
       (B) TYPE: amino acid
       (C) STRANDEDNESS:
       (D) TOPOLOGY: unknown (xi) SEQUENCE DESCRIPTION: SEQ ID NO:42:

Ser Gln Glu Thr Phe Ser Glu Leu Trp Lys Leu
1               5                   10

(2) INFORMATION FOR SEQ ID NO:43:

(i) SEQUENCE CHARACTERISTICS:
       (A) LENGTH: 11 amino acids
       (B) TYPE: amino acid
       (C) STRANDEDNESS:
       (D) TOPOLOGY: unknown (xi) SEQUENCE DESCRIPTION: SEQ ID NO:43:

Ser Gln Glu Thr Phe Ser Gln Leu Trp Lys Leu
1               5                   10

(2) INFORMATION FOR SEQ ID NO:44:

(i) SEQUENCE CHARACTERISTICS:
       (A) LENGTH: 11 amino acids
       (B) TYPE: amino acid
       (C) STRANDEDNESS:
       (D) TOPOLOGY: unknown (xi) SEQUENCE DESCRIPTION: SEQ ID NO:44:

Ser Gln Glu Thr Phe Ser Asn Leu Trp Lys Leu
1               5                   10

(2) INFORMATION FOR SEQ ID NO:45:

(i) SEQUENCE CHARACTERISTICS:
       (A) LENGTH: 11 amino acids
       (B) TYPE: amino acid
       (C) STRANDEDNESS:
       (D) TOPOLOGY: unknown (xi) SEQUENCE DESCRIPTION: SEQ ID NO:45:

Ser Gln Glu Thr Phe Ser Asp Met Trp Lys Leu
1               5                   10

(2) INFORMATION FOR SEQ ID NO:46:

(i) SEQUENCE CHARACTERISTICS:
        (A) LENGTH: 11 amino acids
        (B) TYPE: amino acid
        (C) STRANDEDNESS:
        (D) TOPOLOGY: unknown (xi) SEQUENCE DESCRIPTION: SEQ ID NO:46:

Ser Gln Glu Thr Phe Ser Asp Ile Trp Lys Leu
1               5                   10

(2) INFORMATION FOR SEQ ID NO:47:

(i) SEQUENCE CHARACTERISTICS:
        (A) LENGTH: 11 amino acids
        (B) TYPE: amino acid
        (C) STRANDEDNESS:
        (D) TOPOLOGY: unknown (xi) SEQUENCE DESCRIPTION: SEQ ID NO:47:

Ser Gln Glu Thr Phe Ser Asp Leu Arg Lys Leu
1               5                   10

(2) INFORMATION FOR SEQ ID NO:48:

(i) SEQUENCE CHARACTERISTICS:
        (A) LENGTH: 11 amino acids
        (B) TYPE: amino acid
        (C) STRANDEDNESS:
        (D) TOPOLOGY: unknown (xi) SEQUENCE DESCRIPTION: SEQ ID NO:48:

Ser Gln Glu Thr Phe Ser Asp Leu Phe Lys Leu
1               5                   10

(2) INFORMATION FOR SEQ ID NO:49:

(i) SEQUENCE CHARACTERISTICS:
        (A) LENGTH: 11 amino acids
        (B) TYPE: amino acid
        (C) STRANDEDNESS:
        (D) TOPOLOGY: unknown (xi) SEQUENCE DESCRIPTION: SEQ ID NO:49:

Ser Gln Glu Thr Phe Ser Asp Leu Tyr Lys Leu
1               5                   10

(2) INFORMATION FOR SEQ ID NO:50:

(i) SEQUENCE CHARACTERISTICS:
        (A) LENGTH: 11 amino acids
        (B) TYPE: amino acid
        (C) STRANDEDNESS:
        (D) TOPOLOGY: unknown (xi) SEQUENCE DESCRIPTION: SEQ ID NO:50:

Ser Gln Glu Thr Phe Ser Phe Leu Ile Lys Leu
1               5                   10